United States Patent [19]

Pai

[11] Patent Number: 5,167,877
[45] Date of Patent: Dec. 1, 1992

[54] AIR PURIFIER WITH PERFUME DISPENSING CONTROL

[76] Inventor: Wen-Chung Pai, No. 37, Alley 17, Lane An Tou, Changhua, Taiwan

[21] Appl. No.: 804,406

[22] Filed: Dec. 10, 1991

[51] Int. Cl.⁵ .............................. B01F 3/04; B01F 5/00
[52] U.S. Cl. ..................... 261/18.1; 261/30; 261/83; 261/96; 261/DIG. 65
[58] Field of Search ............... 261/30, DIG. 65, 18.1, 261/83, 96; 422/124

[56] References Cited

U.S. PATENT DOCUMENTS

| | | | |
|---|---|---|---|
| 2,686,944 | 8/1954 | Gubelin | 261/DIG. 65 |
| 3,298,674 | 1/1967 | Gilbertson | 261/30 |
| 4,078,891 | 3/1978 | Madjar | 261/30 |
| 4,601,886 | 7/1986 | Hudgins | 422/124 |
| 4,890,791 | 1/1990 | Hoffman | 261/DIG. 65 |
| 5,023,020 | 6/1991 | Machida et al. | 261/18.1 |

Primary Examiner—Tim Miles
Attorney, Agent, or Firm—Bacon & Thomas

[57] ABSTRACT

An air purifier with perfume dispensing control, comprising a base plate which has a controller and an air pump, a stepped cap mounted on said base plate at the top for holding a plurality of perfume dispensers, a rotary table mounted on said stepped cap and said perfume dispensers at the top, a hood for securing said stepped cap, said perfume dispensers and said rotary table to said base plate, a trigger arm assembly controlled by an electromagnet to alternatively move back and forth causing said rotary table to rotate, and a stop arm assembly to stop said rotary table from reverse rotation. Compressed air from the pump is alternatively delivered to the perfume dispensers while the rotary table is caused to rotate, causing the perfume dispensers to give off different pleasant smells.

3 Claims, 4 Drawing Sheets

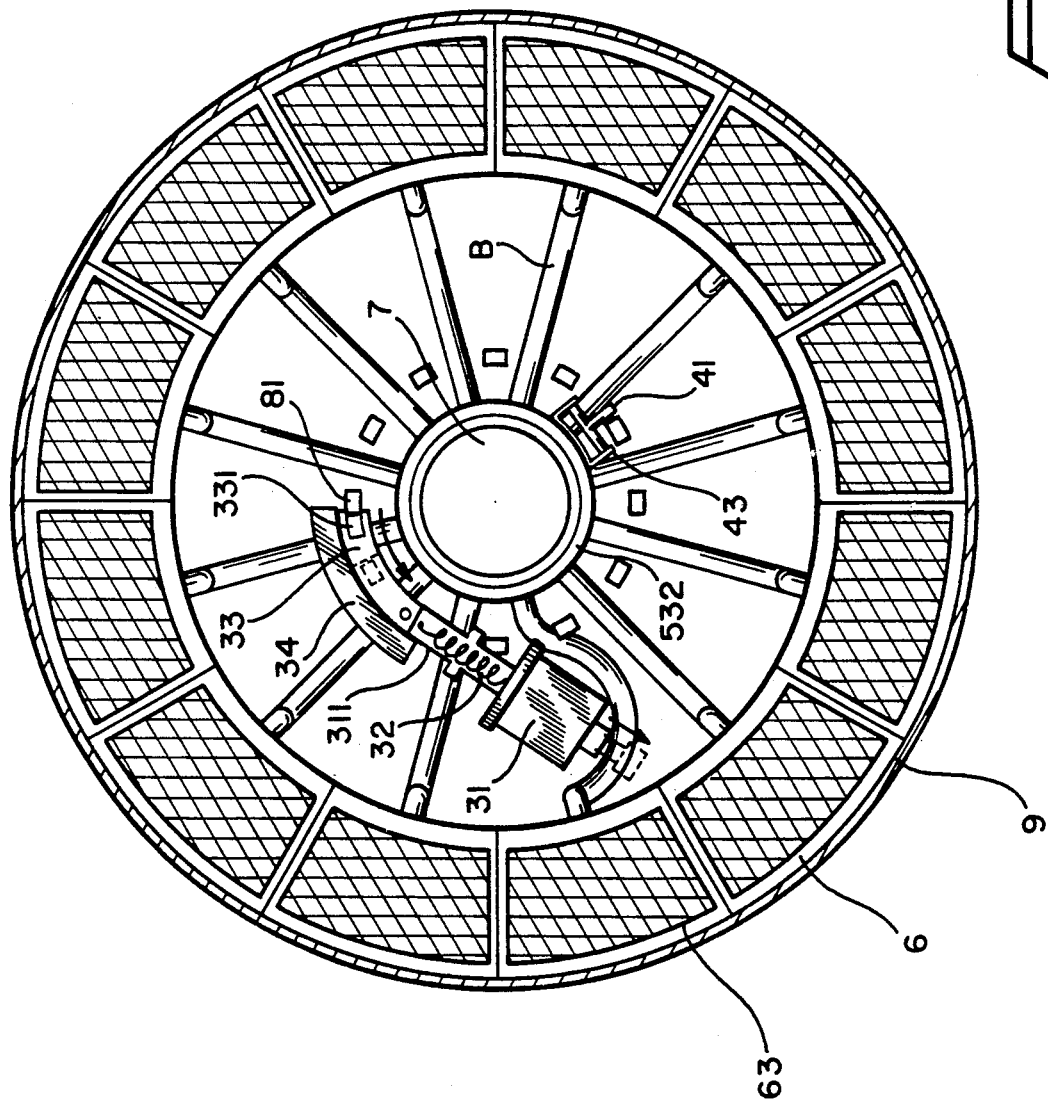

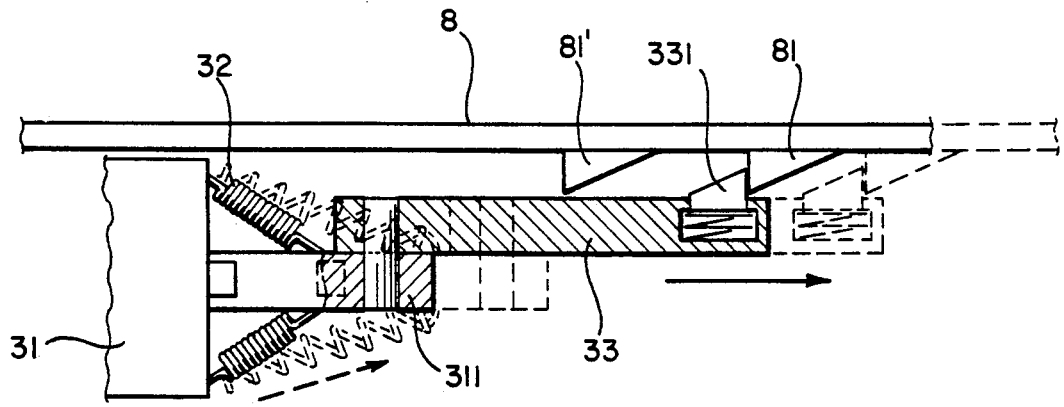
FIG. 3-A
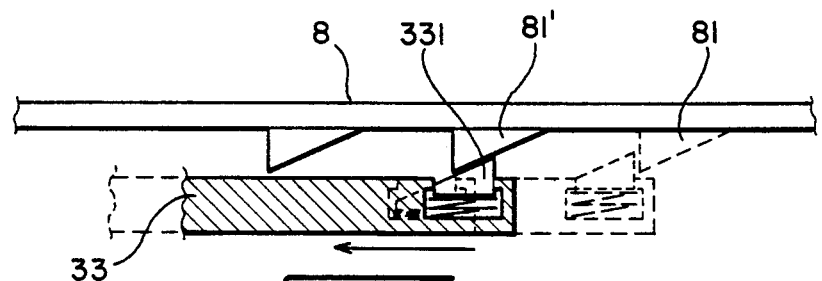
FIG. 3-B
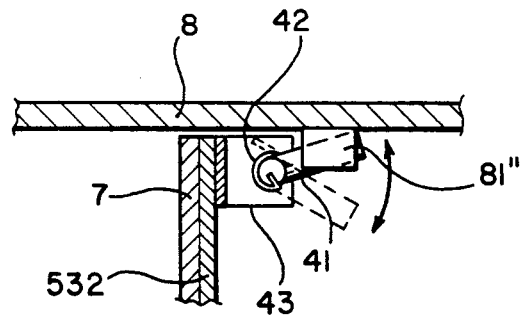
FIG. 3-C
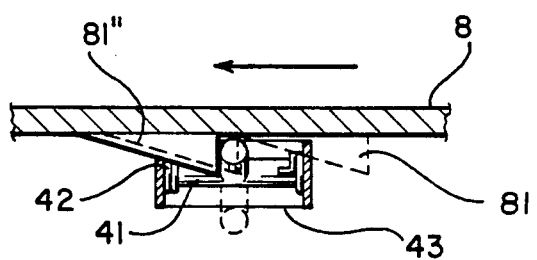
FIG. 3-D

5,167,877

AIR PURIFIER WITH PERFUME DISPENSING CONTROL

BACKGROUND OF THE INVENTION

1. Field of the Invention

The present invention relates to air purifiers and relates more particularly to an air purifier with perfume dispensing control which comprises a plurality of perfume dispensers alternatively controlled to give off different pleasant smells when a rotary table is caused by a trigger arm assembly to rotate with a round hole thereon alternatively aligned with the perfume dispensers.

2. Description of the Prior Art

Air purifier or perfume has been commonly used for deodorizing a lavatory or removing bad smells from a crowded place. Since perfume or aromatic agent generally contains a certain percentage of alcohol, the pleasant smells from a perfume or an aromatic agent in an air purifier may be disappeared quickly. Further, an air purifier general gives off one specific pleasant smell only and, one may be unable to smell out such a specific pleasant smell when one is staying long enough in the place filled with such a specific pleasant smell.

SUMMARY OF THE INVENTION

The present invention has been accomplished to eliminate the disadvantages of the prior art air purifiers. According to one aspect of the present invention, an air purifier is generally comprised of a base plate which has an air pump mounted thereon at the top, a stepped circular cap covered on said base plate at the top which has a trigger arm assembly and a stop arm assembly respectively mounted thereon, a plurality of perfume dispensers mounted on said stepped circular cap, a rotary table fastened in said stepped circular cap and pushed by said trigger arm assembly to rotate above said perfume dispensers, and a ring-shaped hood to secure said rotary table, said perfume dispensers and said stepped circular cap to said base plate. The perfume dispensers each has an air intake hole connected to either round hole on a ring-shaped seat on the stepped circular cap. The rotary table has a hollow, circular block inserted in the ring-shaped seat and pushed by the trigger arm assembly to rotate on the stepped circular cap permitting a hole on the hollow, circular block thereof to be alternatively aligned with the round holes on the ring-shaped seat so that the current of air from the pump can be alternatively blown into the perfume dispensers causing them to give off different pleasant smells one after another. During the operation of the air purifier, the stop arm assembly prohibits the rotary table from reverse rotation.

According to another aspect of the present invention, the trigger arm assembly comprises an extension rod controlled by an electromagnet and two return springs to alternatively move a push rod back and forth along a curved I-track, which push rod has a bevel block on the top edge adjacent to the front end thereof for pushing the rotary table to rotate.

According to still another aspect of the present invention, the perfume dispensers each has a wire gauze filter mounted on the outlet port thereof to filtrate the current of air passing therethrough.

BRIEF DESCRIPTION OF THE DRAWINGS

The foregoing and other objects, features and advantages of the present invention will be best understood from the following description, the appended claims and the accompanying drawings in which:

FIG. 3 is a top view of the preferred embodiment of the present invention;

FIG. 3-A illustrates that the trigger arm assembly is extended out to move the rotary table;

FIG. 3-B illustrates that the trigger arm assembly is moved back to its original position;

FIG. 3-C illustrates that the T-bar of the stop arm assembly is rotated downwards to let a bevel block pass;

FIG. 3-D illustrates that the T-bar of the stop arm assembly is automatically moved upwards to stop the bevel blocks on the rotary table from reverse movement;

DETAILED DESCRIPTION OF THE PREFERRED EMBODIMENT

Figure 1:
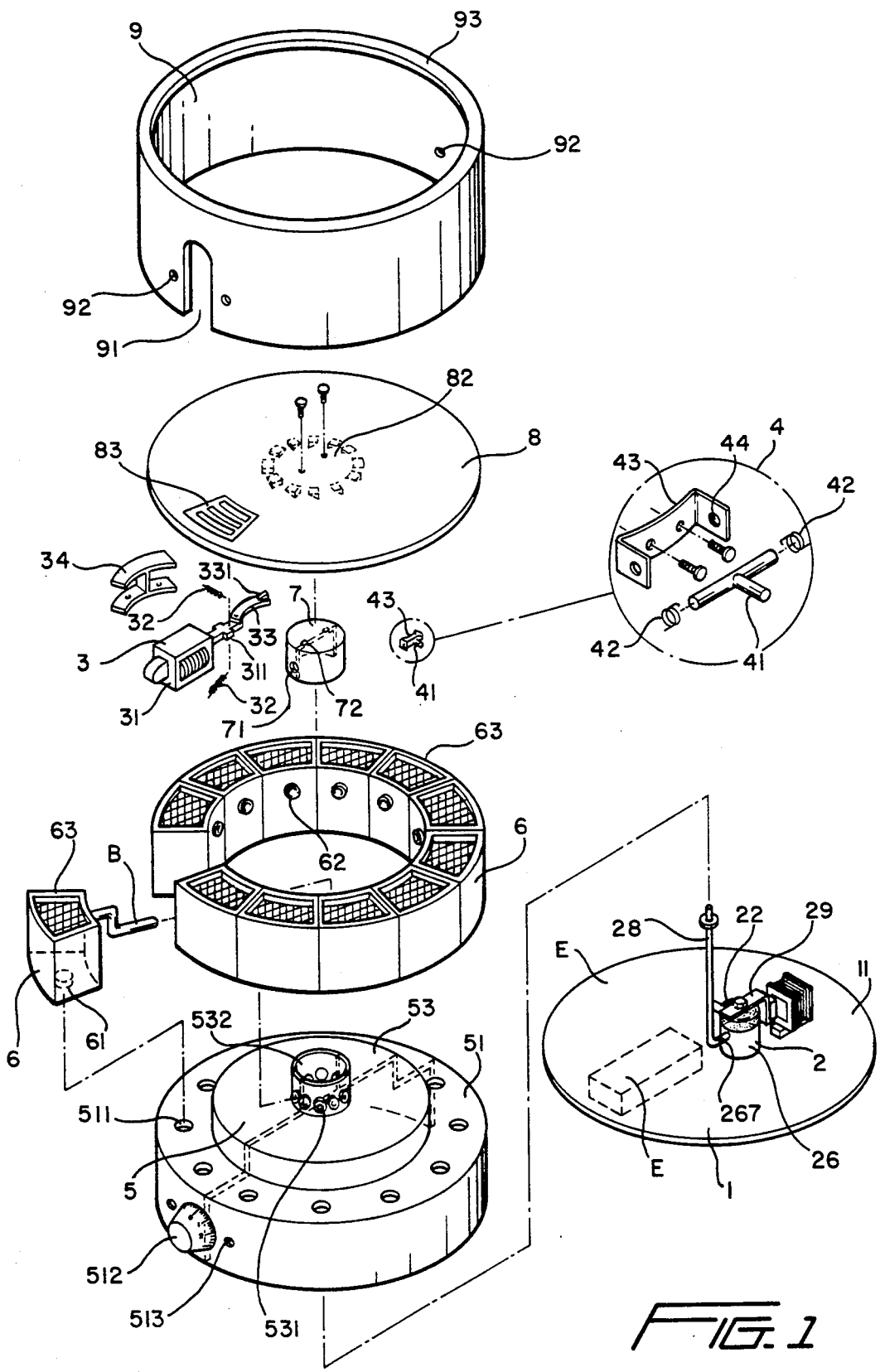
FIG. 1 is an exploded perspective view of the preferred embodiment of the air purifier of the present invention.

Referring to FIGS. 1 through 4, an air purifier as constructed in accordance with the present invention is generally comprised of a base plate 1 having an air pump 2 fastened therein, a stepped circular cap 5 having a trigger arm assembly 3 and a stop arm assembly 4 respectively mounted thereon, a plurality of perfume dispensers 6, a rotary table 8 having a hollow, circular block 7 attached thereto at the bottom, and a hood 9.

Figure 4:
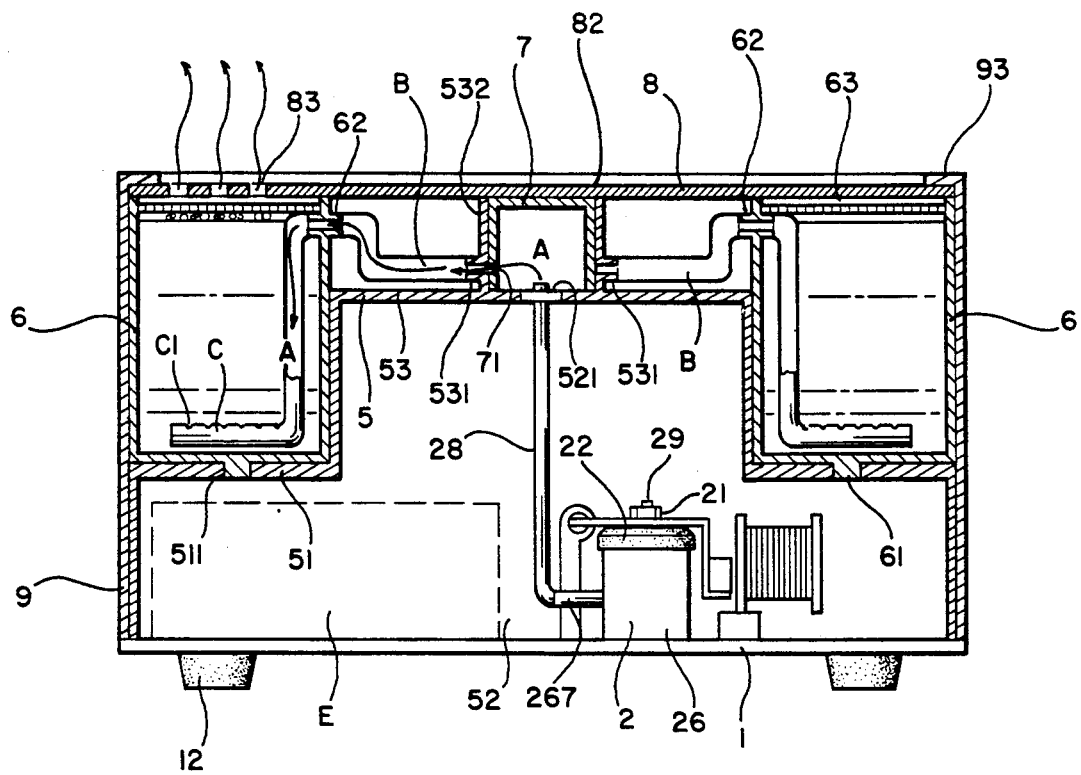
FIG. 4 is a sectional view of the preferred embodiment of the present invention taken in longitudinal direction.
Figure 2:
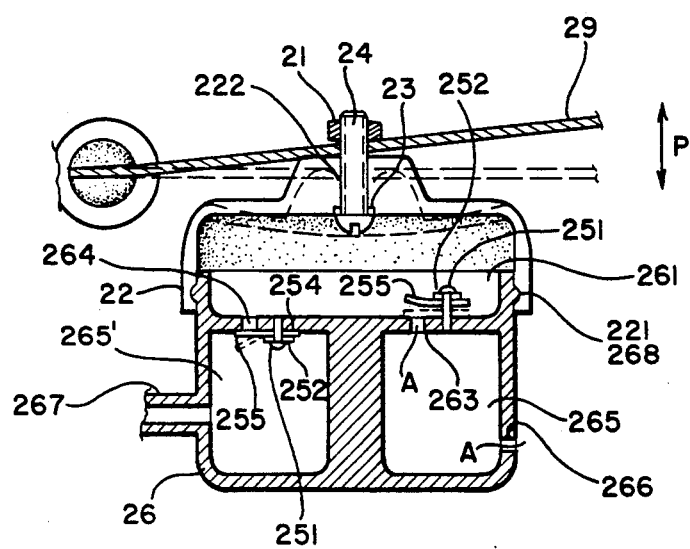
FIG. 2 is a schematic drawing showing the operation of the air pump.

As illustrated in FIGS. 1 and 4, the base plate 1 has stands 12 on the bottom edge thereof and a bearing surface 11 at the top for holding a controller E and the air pump 2. As illustrated in FIGS. 1 and 2, the air pump 2 is comprised of a screw nut 21, an expansion cap 22 having a through-hole 222 at the center and an annular groove 221 on the inner wall surface, a sealing ring 23, a plurality of screws 24, a plurality of lock pins 251, a plurality of semi-circular sealing caps 253 each of which having a round hole 252, a plurality of curved flaps 255 each of which having a round hole 254, and an air container 26. The air container 26 comprises a recess 261 at the top with a locating hole 262, an air inlet 263 and an air outlet 264 respectively made thereon, a circular flange 268 around the peripheral surface thereof at an upper position, a bolt hole 269 on the bottom edge thereof at the center 265' at the bottom, wherein the inlet chamber 265 has a plurality of air intake holes 266 at one side adjacent to the bottom edge thereof; the outlet chamber 265' has a conduit 267 connected thereto at one side. The trigger arm assembly 3 comprises an electromagnet 31, an extension rod 311 controlled by said electromagnet 31 and secured in place by return springs 32, a curved push rod 33 secured to said extension rod 311 at the front, said push rod 33 having a bevel block 331 attached thereto at the top adjacent to the front end thereof, and a curved I-track 34 spaced from said push rod 33 at one side. The stop arm assembly 4 comprises a T-bar 41 which has two torsional springs 42 attached thereto at two opposite ends, and a fastening frame 43 which has two round holes 44 at two opposite ends. The two torsional springs 42 are respectively fastened in the two round holes 44 on the fastening frame 43, and therefore, the T-bar 41 is constantly maintained in a vertical position. The stepped circular cap 5 defines therein a receiving chamber 52 and is comprised of an upper step 53 which has a center hole 521 at the center, a ring-shaped seat 532 raising around the center hole 521, which ring-shaped seat 532 has a plurality of round holes 531 around the peripheral surface thereof, and a lower step 51 which has a plurality of round holes 511 at the top, a timer 512 and a plurality of bolt holes 513 at one side. The perfume dispensers 6 each is made from a sector-like container having a stub rod 61 extending from the bottom edge thereof at the center, an outlet port 63 at the top, a round hole 62 at one side, and an internal pipe C which has a plurality of outlet holes C1 extending from the round hole 62 at the inside. The hollow, circular block 7 is made in a cap-like hollow structure and fixedly attached to the rotary table 8 at the bottom, having a round hole 71 at one side and two bolt holes 72 at the top. The rotary table 8 has a plurality of bevel blocks 81 on the bottom edge thereof around a circle, two bolt holes 82 at the top, and a plurality of slots 83 at a suitable location. The hood 9 is made from a ring-shaped plate, having a notch 91 and a plurality of bolt holes 92 on the side wall thereof at suitable locations and an inward flange 93 around the topmost edge thereof.

Assembly process of the present invention is outlined hereinafter with reference to FIG. 4. The stepped cap 5 is covered on the base plate 1 at the top with the air pump 2 and the controller E received in the receiving chamber 52 and with an air pipe 28 connected between the conduit 267 and the center hole 521. The perfume dispensers 6 are respectively mounted on the stepped cap 5 by inserting the stub rods 61 thereof into the round holes 511 on the lower step 51 of the stepped cap 5. Then, connect the round holes 62 on the perfume dispensers 6 to the round holes 531 on the ring-shaped seat 532 by flexible pipes B. The rotary table 8 is then mounted on the perfume dispensers 6 at the top with the hollow, circular block 7 inserted in the ring-shaped seat 532 permitting the bevel blocks 81 to be moved or stopped by the trigger arm assembly 3 and the stop arm assembly 4. Then, the hood 9 is mounted on the rotary table 8 and secured to the stepped cap 5 with the timer 512 protruding through the notch 91.

Referring to FIGS. 2, 3, and 3-A through 3-D, when a current of air A enters the inlet chamber 265 through the air intake holes 266, the flap 255 and the sealing cap 253 on the air inlet 263 are pushed to open, and therefore, the current of air A is allowed to enter the recess 261. Once the the inlet chamber 265 and the recess 261 are filled with air, an L-shaped pressure plate 29 is caused by electromagnetic force to oscillate back and forth. When the L-shaped pressure plate 29 is pressed down, the expansion cap 22 is squeezed, the flap 255 and sealing cap 253 on the air inlet 263 are pushed to close the air inlet 263 and at the same time, the flap 255 and the sealing cap 253 on the air outlet 2654 are pushed to open the air outlet 264 (as shown in FIG. 2) permitting the current of air A to pass through the conduit 267 and the air pipe 28 into the hollow, circular block 7. Further, the controller E is controlled to trigger the electromagnet 31 at a fixed time, causing the push rod 33 to displace along the curved I-track 34. When the push rod 33 is moved forward, the bevel block 331 on the push rod 33 will push either bevel block 81 on the rotary table 8 causing the rotary table 8 to rotate (as shown in FIG. 3-A). Once the push rod 33 has been moved forward to a fixed range, the electromagnet 31 is disabled, and therefore, the push rod 33 is immediately pulled back to its original position by the return springs 32. When the bevel block 331 is moved backwards its top sloping surface is moving through the bottom sloping surface of a next bevel block 81' on the rotary table 8, and therefore, the rotary motion of the rotary table 8 will not be interfered (see FIG. 3-B). At the same time, the T-bar 41 of the stop arm assembly 4 is stopped at the vertical edge of another bevel block 81" on the rotary table 8 to stop the rotary table 8 from reverse rotation (see FIG. 3-D). When the push rod 33 forces the bevel block 81 to move, the T-bar 41 will be forced to rotate downwards so as to pass through the bevel block #81. Once the T-bar 41 passes through the bevel block #81, it is immediately moved upwards to stop at the vertical edge of the bevel block #81 (see FIG. 3-C). During the rotary motion of the rotary table 8, the round hole 71 on the hollow, circular block 7 will be alternatively aligned with the round holes 531 on the ring-shaped seat 532 permitting the current of air A from the air container 26 to passes through the flexible pipes B into the perfume dispensers 6 one after another. The perfume dispensers 6 are respectively contained with different perfumes which produce different pleasant smells. Therefore, when a current of air passes through a flexible pipe B into the internal tube C in either perfume dispenser 6, a specific pleasant smell will be carried out of the perfume dispenser 6. While the pump 2 is continuously operated, different pleasant smells will be alternatively produced.

I claim:

1. An air purifier with perfume dispensing control, comprising:

a base plate having stands on the bottom edge thereof, a controller and an air pump on the top edge thereof, said air pump comprised of a recess at the top covered by an expansion cap, an inlet chamber and an outlet chamber at the bottom, said recess having holes respectively connected to said inlet and outlet chambers by flap valves, said inlet chamber having air intake holes for taking in outside air, said outlet chamber having an outlet port at one side;

a stepped circular cap mounted on said base plate at the top, said stepped circular cap being comprised of an upper step and a lower step, said upper step having a center hole connected to said outlet port on said outlet chamber by an air pipe and a ring-shaped seat at the top, said ring-shaped seat having a plurality of round holes around the peripheral surface thereof, said lower step having a plurality of round holes at the top and a timer at one side;

a plurality of perfume dispensers respectively mounted on said lower step around said upper step for holding different aromatic agents, said perfume dispensers each having a stub rod at the bottom inserted in either round hole on said lower step, an air intake hole at one side connected to either round hole on said ring-shaped seat by a flexible pipe, and an outlet port at the top;

a rotary table rotatably mounted on said perfume dispensers at the top, said rotary table having a hollow, circular block at the bottom inserted in said ring-shaped seat, a slotted port for the passing therethrough and a plurality of bevel blocks on the bottom edge thereof around a circle, said hollow, circular block having a round hole moved to alternatively aligned with the round holes on said ring-shaped seat;

a hood made from a ring-shaped plate and sleeved on said rotary table, said perfume dispensers and said stepped cap, said hood having a notch on the side wall thereof, through which a timer is exposed to the outside for operation, and an inward flange to hold said rotary table in place;

a trigger arm assembly mounted on said stepped cap at the top and controlled by said controller to push said bevel blocks causing said rotary table to rotate;

a stop arm assembly mounted on said stepped cap at the top to stop said rotary table from reverse rotation, said stop arm assembly comprising a T-bar having two opposite ends secured to a fastening frame by two torsional springs; and wherein said pump is intermittently compressed by magnetostriction oscillation to send a current of air out of said outlet chamber through said outlet port while said rotary table is caused to rotate by said trigger arm assembly, permitting the current of air to enter either perfume dispenser for blowing the pleasant smell of the aromatic agent contained therein out of the perfume dispenser to which the round hole on said hollow, circular block is aligned.

2. The air purifier of claim 1, wherein said trigger arm assembly comprising an electromagnet controlled to operate by said controller, an extension rod controlled by said electromagnet to move back and forth alternatively, return springs to secure said extension rod in place, a curved push rod secured to said extension rod at the front, said push rod having a bevel block attached thereto at the top adjacent to the front end thereof for pushing either bevel blocks on said rotary table causing said rotary table to rotate, and a curved I-track for guiding said push rod.

3. The air purifier of claim 1, wherein said perfume dispensers each has a wire gauze filter covered on said output port to filtrate the air passing therethrough.

* * * * *